United States Patent
Reid (12)

(10) Patent No.: US 6,322,994 B1
(45) Date of Patent: Nov. 27, 2001

(54) METHOD OF FREEZE-DRYING ORGANISMS

(75) Inventor: Mark Reid, Dorset (GB)

(73) Assignee: Genetix Limited, Dorset (GB)

( * ) Notice: Subject to any disclaimer, the term of this patent is extended or adjusted under 35 U.S.C. 154(b) by 0 days.

(21) Appl. No.: 09/433,356

(22) Filed: Nov. 4, 1999

(51) Int. Cl.$^7$ ............... C12Q 1/02; A01N 1/00; C12M 1/00
(52) U.S. Cl. ............ 435/29; 435/1.3; 435/40.5; 435/284.1; 435/288.4; 435/305.2; 435/307.1
(58) Field of Search ................ 435/1.3, 29, 33, 435/40.51, 284.1, 288.4, 305.2, 307.1

(56) References Cited

U.S. PATENT DOCUMENTS

| | | | | |
|---|---|---|---|---|
| 4,879,239 | * | 11/1989 | Daggett et al. | 435/252.1 |
| 5,858,770 | | 1/1999 | Perlman | 435/305.3 |
| 5,925,511 | * | 7/1999 | Fuhr et al. | 435/1.3 |

OTHER PUBLICATIONS

Franks; "Effective Freeze–Drying: A Combination of Physics, Chemistry, Engineering and Economics"; The Institute of Marine Engineers; 1994–1995; pp. 32–39.

A Guide to Freeze Drying for the Laboratory; An Industry Service Publication; 1998; pp. 3–11.

LESLIE et al., "Trehalose And Sucrose Protect Both Membranes and Proteins in Intact Bacteria During Drying", *Applied And Environmental Microbiology*, vol. 61(10):3592–3597, (1995).

BARBAREE et al., "Problems In Freeze–Drying: II. Cross-Contamination During Lyophilization", *Developments in Industrial Microbiology*, vol. 26:407–409, (1984).

* cited by examiner

*Primary Examiner*—David A. Redding
(74) *Attorney, Agent, or Firm*—Foley & Lardner

(57) ABSTRACT

A method is provided for freeze-drying multiple samples of viable microorganisms which method comprises:

(i) providing a container comprising multiple wells;

(ii) dispensing multiple liquid samples, each sample comprising a viable microorganism, into separate wells of the container;

(iii) placing the container in a freeze-drying apparatus; and (iv) freeze-drying the samples present in the wells under conditions that substantially maintain the viability of the microorganisms.

Also provided is a container comprising multiple wells, each well comprising a viable freeze-dried sample of a microorganism.

10 Claims, 2 Drawing Sheets

METHOD OF FREEZE-DRYING ORGANISMS

FIELD OF THE INVENTION

The present invention relates to the freeze-drying of multiple samples of microorganisms such as bacteria in a multiwell format that may be stored and used at room temperature.

BACKGROUND TO THE INVENTION

Freeze-drying has been used in various applications for several years, such as in the food industry and pharmaceutical industry. Freeze-drying has also been used to prepare microorganisms such as bacteria for long term storage. In particular microorganism depositories such as the American Type Culture Collection often freeze-dry cultures for distribution since properly freeze-dried microorganisms remain viable at room temperature and can be transported without the need for solid carbon dioxide.

However, freeze-drying equipment is too expensive for day-to-day use by laboratory scientists who tend to keep microorganisms either as glycerol stocks at $-80°$ C. or in liquid nitrogen. Both forms of storage are relatively expensive and also carry the risk of loss of sample viability if the equipment fails. Nonetheless, a significant amount of storage space in $-80°$ C. freezers is given over to the storage of bacterial strains as glycerol stocks, for example to store bacterial colonies selected during cloning procedures. There is therefore a need to provide laboratory scientists with a means of storing large numbers of different microorganisms in an easily accessible format that does not require expensive freezer space.

SUMMARY OF THE INVENTION

We have now found that it is feasible to freeze-dry multiple samples of different microorganisms in microtiter plates, without cross contamination, resulting in microtiter plate "libraries" of microorganisms that may be stored at room temperature at high density. The resulting saving in high cost freezer space is likely to compensate for any initial outlay of freeze-drying equipment. Furthermore, the use of a room temperature microtiter plate format is more compatible with recent advances in automated machinery for screening bacterial libraries picked by machine.

Accordingly the present invention provides a method for freeze-drying multiple samples of viable microorganisms which method comprises:

(i) providing a container comprising multiple wells;

(ii) dispensing multiple liquid samples, each sample comprising a viable microorganism, into separate wells of the container;

(iii) placing the container in a freeze-drying apparatus; and (iv) freeze-drying the samples present in the wells under conditions that substantially maintain the viability of the microorganisms.

Preferably the container is a microtiter plate.

In a preferred embodiment, the viable microorganisms have been grown prior to freeze-drying in a culture medium comprising an excipient and the microorganisms are freeze-dried in said culture medium.

Preferably the wells of the container are provide with sterile sealing means. More preferably, the sealing means permit removal of a portion of a freeze-dried microorganism sample from a well whilst maintaining a sterile seal.

The present invention further provides a container comprising multiple wells, each well comprising a viable freeze-dried sample of a microorganism. Preferably, the container is a microtiter plate.

In a preferred embodiment, the container further comprises sterile sealing means for each well. Preferably the sterile sealing means allow the removal of a portion of a freeze-dried microorganism sample from a well whilst maintaining a sterile seal.

The present invention also provides a container of the invention obtained by the method of the invention.

DETAILED DESCRIPTION OF THE INVENTION

A. Containers

Figure 1:
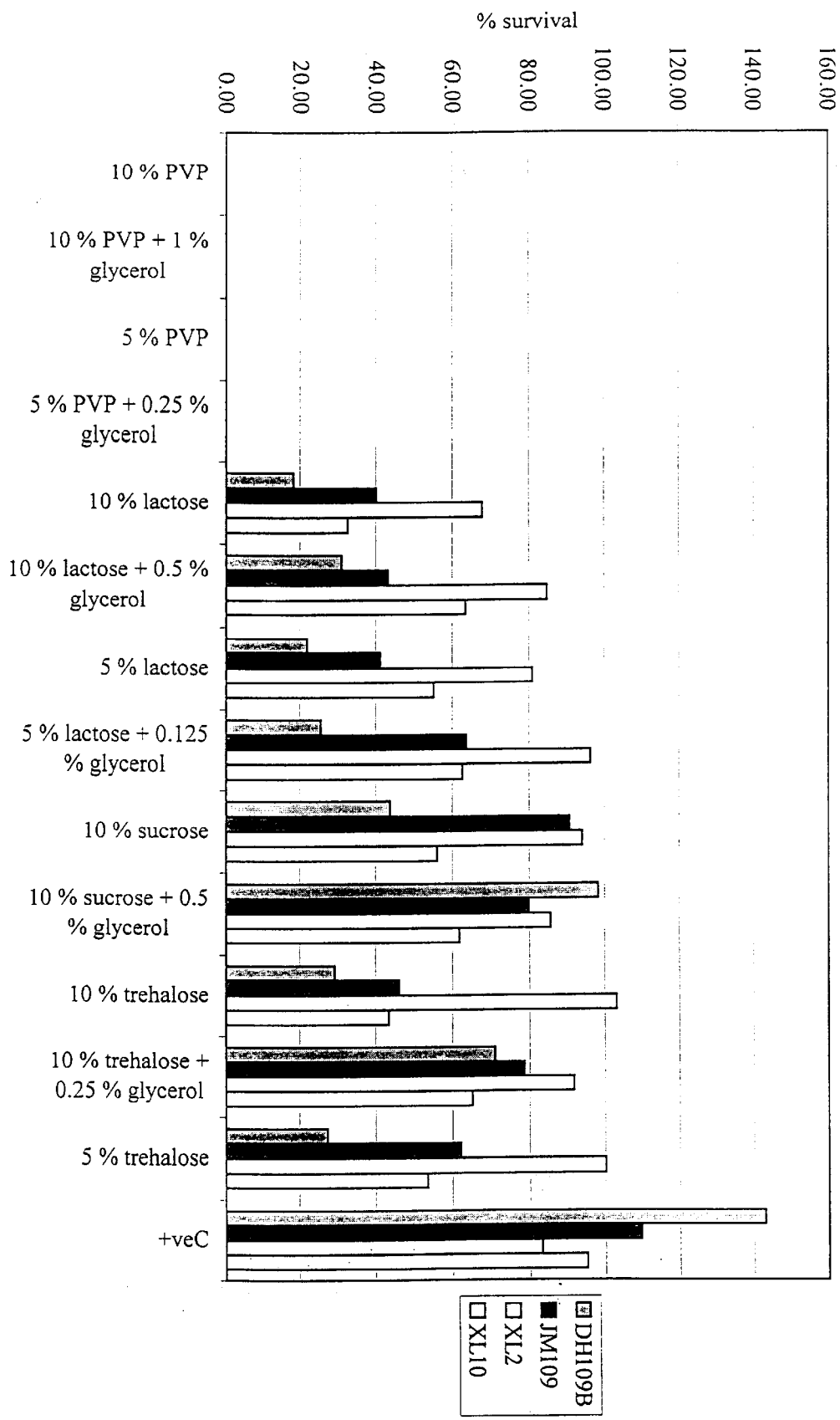
FIG. 1 is a graph showing % survival for *E. coli* strains freeze-dried in various excipients.

A container suitable for use according to the present invention comprises multiple wells into which substantially liquid samples may be dispensed. "Multiple" means two or more but preferably the number of wells is at least 6, 12 or 24 more preferably at least 96, such as 384. Examples of suitable containers include microtiter plates and multi-well tissue culture plates. Microtiter plates are preferably of the rigid type rather than the flexible type. Specific examples of microtiter plates include 96 and 384 well plates made by Nunc, Costar and Greiner and 96, 384 and 1536 well plates made by Genetix. The "well" is intended to encompass, for example, an indentation in a substantially planar solid substrate that is suitable for receiving a volume of liquid such that the liquid can be kept physically separate from the contents of a neighboring well.

The container is typically formed from a single piece of plastic, such as polycarbonate, by extrusion molding. The container may optionally have a separate lid, as is common for example with tissue culture multi-well plates. Preferably the container is not substantially made of glass.

Once freeze-drying is completed, the container is typically sealed to prevent moisture being absorbed by the freeze-dried sample and typically to keep the freeze-dried samples sterile. Examples of methods of sealing the containers include the use of vacuum sealed plastic packaging or sealing the containers with plastic or foil and placing the sealed container in a plastic bag, preferably together with a desiccant such as silica gel. Shrink-wrapping may also be suitable. Where the container has a preformed lid, the gap between the lid and the base of the container may typically be sealed with an elastic material such as Parafilm™ or Nescofilm™. In addition, it may be desirable to seal the container in an inert atmosphere such as nitrogen.

It is preferred to use sterile sealing means that allow the removal of a portion of a sample from any particular well whilst maintaining the integrity of any remaining sample in that well. For example, the sterile sealing means may comprise a substantially moisture impermeable material that allows a needle or pin to be inserted through the membrane and into contact with the freeze-dried sample but which, when the needle or pin is removed, reseals such that a contiguous, substantially moisture impermeable seal is reformed. The material will typically have elastic properties. A suitable material includes rubber, such as the rubber used to seal vials of freeze-dried pharmaceutical products. The sealing means may be provided as a contiguous sheet that seals multiple wells or individually for each well.

B. Microorganisms

The term "microorganism" includes prokaryotes and eucaryotes such as yeast, fungi and animal and plant cells capable of being propagated in culture, such as immortalised cell lines. Examples of procaryotes include eubacteria and archaebacteria. Eubacteria include gram negative bacteria such as Escherichia sp. (e.g. *E. coli*), Neisseria sp., Campylobacter sp., Haemophilus sp., Streptococcus sp. and Staphylococcus sp. and gram positive bactera such as Bacillus sp. (e.g. *B. subtilis*). Preferably the microorganism is a eubacterium.

Microorganisms are typically grown prior to freeze-drying in standard culture medium appropriate to that specific type of microorganism, such as LB broth for *E. coli*. In a preferred embodiment of the present invention, the microorganisms are grown in the presence of an excipient used to raise the glass transition point (Tg) of the sample, as discussed below. Since these excipients often increase the osmotic potential of the growth medium to unsuitable levels, it may be necessary to adjust the composition of the growth medium to compensate, for example by decreasing the salt content.

C. Freeze-drying

Freeze-drying involves the removal of water or other solvent from a frozen product by a process called sublimation. Sublimation occurs when a frozen liquid goes directly to the gaseous state without passing through the liquid phase. Freeze-drying is a routine technique used in the art and suitable equipment is available from commercial sources such as Labconco (Kansas City, Mis., USA). However, for completeness, a brief description of the freeze-drying process is set out below, some of which is based on information provided in "A Guide to Freeze-drying for the Laboratory"—an industry service publication by Labconco, 1998. See also Franks, F. (1994), Effective freeze-drying: a combination of physics, chemistry, engineering and economics. Proc. Inst. Refrigeration 91: 32–39.

The freeze-drying process consists of three stages: prefreezing, primary drying and secondary drying.

Prefreezing: the material to be freeze-dried must be adequately prefrozen. It is important in freeze-drying to prefreeze the product below the glass transition point (Tg). As the temperature of the sample is lowered, the water in the sample freezes, increasing the concentration of solutes in the sample and increasing the viscosity of the mixture. As the viscosity increases steeply, the rate of freezing reduces, eventually stopping altogether. The residual mixture, including the ice, undergoes a glass transition, where the viscosity increases by many orders of magnitude over a narrow temperature interval. Structurally, the sample in then in the form of an amorphous solid and is described as a glass. This transition from a super-saturated, frozen aqueous solution of very high viscosity to a brittle solid is operationally characterized by a glass transition temperature ($T_g$). The $T_g$ for a sample can be determined by methods known in the art, such as differential scanning calorimetry or thermomechanical analysis.

However the $T_g$ for samples of microorganisms in standard culture medium is often too low for practical purposes and must be raised by the addition of excipients. Suitable excipients include glucose, sucrose, maltose, lactose, trehalose, raffinose, maltotriose, stachyose and dextran. Other suitable excipients are known in the art. Preferably the excipient is added in such an amount as to raise the $T_g$ to about from −20 to −40° C. The amounts may vary between types of sample but may readily be determined by the person skilled in the art. A suitable amount is typically from 5 to 15% w/v, such as from 7.5 to 12.5% w/v.

Primary drying: after prefreezing the sample, conditions must be established in which ice can be removed from the frozen product by sublimation. Samples are typically pre-frozen to well below their $T_g$ and then the temperature is raised to just below the $T_g$. The samples are then subjected to reduced pressure in a vacuum chamber. At this point the freeze-drying process begins.

Secondary drying: after primary freezing is completed, all the frozen water has sublimed. However, non-frozen bound moisture is still present in the product. Continued drying at a higher temperature is required to drive off the residual moisture by evaporation.

Several types of freeze-drying methods are currently in use including the manifold method, the batch method and the bulk method. It is preferred according to the present invention to use an apparatus suited to the batch method, such as a tray dryer.

Samples of microorganisms may be grown in the container prior to freeze-drying or grown in a separate vessel and dispensed into the wells of the container. Each well of the container may comprise a different microorganism, such as a different clone from a library without a significant risk of cross-contamination.

If a suitable excipient has not yet been added then it is now added to the samples in the wells, or to the sample prior to transfer into the wells, and mixed. Once the excipient has been added, if not already added, the container may be frozen at a temperature below the $T_g$ (e.g. in a −80° C. freezer) and maintained at that temperature until it is freeze-dried, if it cannot be freeze-dried immediately. The container is then placed in the freeze-drying apparatus and freeze-dried using standard techniques. Once freeze-drying is complete, the container is typically sealed as described above. The container may then be kept at room temperature, or below room temperature, as required, such that the viability of the microorganisms is maintained.

The term "viablity" refers to the ability of a culture of microorganisms to grow. For example, a "viable" sample is comprised of live organisms that are capable of metabolism and growth. Consequently, a freeze-dried sample is viable if it can be revived, such as by rehydration, and grown in a suitable median. Preferably, the sample remains viable for at least one month, preferably at least two, three or six months, more preferably at least a year at room temperature (herein defined as 18° C. for the purposes of the present invention).

In general, cryoprotectants such as DMSO and glycerol, which are often used to protect the cells from damage during the freezing process, are not required in the method of the invention, but may be added if necessary. Preferably cryoprotectants are included in the sample medium, more preferably glycerol is included in the sample medium, prior to freezing. In a particularly preferred embodiment, at least 0.1% glycerol v/v is included, preferably at least 0.2%. Typically, not more than 10% glycerol is added, preferably not more than 5 or 1% glycerol.

D. Uses

The method of the invention may be used to freeze-dry multiple samples of microorganisms such as libraries of clones picked from agar plates for use at a later date. It is envisaged that the method of the invention will be useful in obtaining freeze-dried libraries of microorganisms obtained by cloning techniques used in the field of molecular biology. The libraries may subsequently be used in further screening techniques. By way of example, bacterial colonies may be picked on the basis of comprising a recombinant plasmid encoding an antibiotic resistance gene from antibiotic containing agar plates, grown in microtiter plates and then freeze-dried. The freeze-dried samples may then subsequently be revived, such as by rehydration, and used in nucleic acid detection procedures to identify specific clones. Alternatively, or in addition, selected clones may be cultured and freeze-dried for later molecular characterization.

Partially or fully preselected libraries of clones that are freeze-dried in a multiwell plate format and which remain viable when stored at room temperature may be an extremely convenient means of distributing libraries of clones on a commercial and/or non-commercial basis rather than simply providing non-preselected libraries in a single vial that the researcher would then need to screen themselves.

The invention will now be described with reference to the examples which are illustrative only and non-limiting.

EXAMPLES

Viability Testing of Freeze-dried Bacteria

Methods

Four strains of *E. coli* (DH10B, JM109, XL2 and XL10), transformed with pUC18/19, were grown in LB broth containing ampicillin (50 $\mu$g.ml$^{-1}$). An aliquot of each culture was made up to 8% glycerol and stored at −80° C. as a positive control. 5 ml aliquots of the cells were pelleted by centrifuging at 4000 g for 5 min and resuspended in 5 ml of LB broth. Appropriate dilutions, in LB broth, of the resuspended cells were plated out on LB agar containing ampicillin (50 $\mu$g.ml$^{-1}$) to determine the viable cell count.

5 ml aliquots of each of the strains of *E. coli* were pelleted by centrifugation at 4000 g for 5 min, resuspended in 5 ml of LB supplemented with each of 13 excipients (Graph 1) and 50 $\mu$l aliquots were pipetted into 384-well plates, using a separate plate for each strain. As a control for well to well contamination, 50 $\mu$l of LB supplemented with each excipient was pipetted into a well adjacent to one containing culture. A negative control plate was prepared with 50 $\mu$l aliquots of LB supplemented with each excipient pipetted into a series of wells as a control for bacterial contamination of the excipient solution. The plates were frozen at −80° C. and transported to a freeze-drying facility for freeze-drying. Following freeze-drying, the plates were stored at 4° C. in sealed bags for 17 days prior to viability testing.

For each plate, 50 $\mu$l of sterile H$_2$O was added to 1 well for each excipient, plus 2 of the control wells from each of the plates containing bacteria, and incubated at room temperature for 10 min to rehydrate the freeze-dried culture. The cultures were serially diluted in LB broth containing ampicillin (50 $\mu$g.ml$^{-1}$) and 100 $\mu$l of the appropriate dilution was plated out on LB agar containing ampicillin (50 $\mu$g.ml$^{-1}$) to determine the viable cell count.

Results

FIG. 1 (see also Tables 1 and 2) shows the % survival for each strain of bacteria in each of the excipients. Of the 8 controls for well to well contamination, all but 1 were negative and all the samples from the negative control plate were negative.

Conclusions

Although there was a degree of experimental error in the results, it is clear that PVP is not suitable as an excipient for the *E. coli* strains tested. The excipients which gave the best results for all the bacterial strains were 10% sucrose+0.5% glycerol and 10% trehalose+0.25% glycerol.

Figure 2:
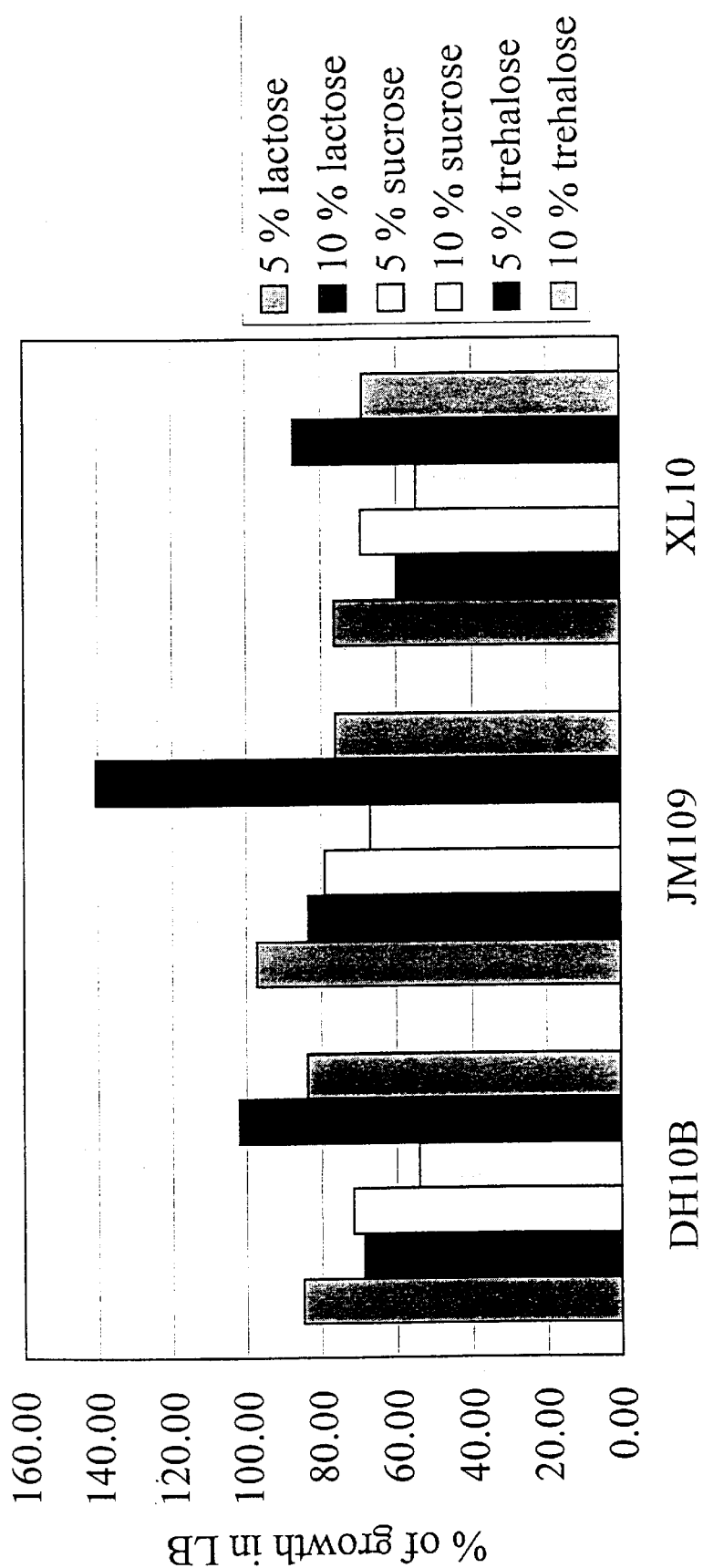
FIG. 2 is a graph showing bacterial growth in different excipients as a % of that in LB.

The bacteria were cultured initially in standard medium, rather than the excipient they were to be freeze-dried in, because previous work had shown that bacterial growth was inhibited in LB+10% sucrose or 10% trehalose. This may be due to osmotic effects. However the results shown in FIG. 2 indicate that in fact satisfactory bacterial growth occurs in the presence of all three excipients tested: lactose, sucrose and trehalose. In particular growth was not particularly affected by LB+10% lactose, presumably because the presence of an intact lacZ gene on the pUC18/19 plasmid allowed the bacteria to metabolise lactose, although typically in practice when dealing with recombinant plasmids, the lacZ gene is disrupted. However, it should be possible to offset the osmotic effects of the excipient by modifying the standard medium to compensate.

These results shown in FIG. 1 demonstrate that all 4 strains of bacteria tested can survive freeze-drying in 384-well plates. Furthermore, this format, despite having a relatively high density of different samples, is capable of maintaining sample integrity (avoiding cross-contamination).

TABLE 1

| Strain | Excipient* | Dilution | No. colonies | Cells/ml. | % survival |
|---|---|---|---|---|---|
| JM109 | 1 | 1.00E-06 | 0 | 0.00E+01 | 0.00 |
| JM109 | 3 | 1.00E-06 | 0 | 0.00E+01 | 0.00 |
| JM109 | 5 | 1.00E-06 | 0 | 0.00E+01 | 0.00 |
| JM109 | 7 | 1.00E-06 | 0 | 0.00E+01 | 0.00 |
| JM109 | 9 | 1.00E-06 | 80 | 8.00E+08 | 40.00 |
| JM109 | 11 | 1.00E-06 | 86 | 8.60E+08 | 43.00 |
| JM109 | 13 | 1.00E-06 | 82 | 8.20E+08 | 41.00 |
| JM109 | 15 | 1.00E-06 | 127 | 1.27E+09 | 63.50 |
| JM109 | 17 | 1.00E-06 | 181 | 1.81E+09 | 90.50 |
| JM109 | 19 | 1.00E-06 | 159 | 1.59E+09 | 79.50 |
| JM109 | 21 | 1.00E-06 | 92 | 9.20E+08 | 46.00 |
| JM109 | 23 | 1.00E-06 | 157 | 1.57E+09 | 78.50 |
| JM109 | 24 | 1.00E-06 | 124 | 1.24E+09 | 62.00 |
| JM109 | +ve | 1.00E-06 | 184 | 2.19E+09 | 109.50 |
| JM109 -veC | 1 | 1.00E-01 | 0 | 0.00E+01 | |
| JM109 -veC | 9 | 1.00E-01 | 0 | 0.00E+01 | |
| XL2 | 1 | 1.00E-06 | 0 | 0.00E+01 | 0.00 |
| XL2 | 3 | 1.00E-06 | 0 | 0.00E+01 | 0.00 |
| XL2 | 5 | 1.00E-06 | 0 | 0.00E+01 | 0.00 |
| XL2 | 7 | 1.00E-06 | 0 | 0.00E+01 | 0.00 |
| XL2 | 9 | 1.00E-06 | 88 | 8.80E+08 | 67.69 |
| XL2 | 11 | 1.00E-06 | 110 | 1.10E+09 | 84.62 |
| XL2 | 13 | 1.00E-06 | 105 | 1.05E+09 | 80.77 |
| XL2 | 15 | 1.00E-06 | 125 | 1.25E+09 | 96.15 |
| XL2 | 17 | 1.00E-06 | 122 | 1.22E+09 | 93.85 |
| XL2 | 19 | 1.00E-06 | 111 | 1.11E+09 | 85.38 |
| XL2 | 21 | 1.00E-06 | 134 | 1.34E+09 | 103.08 |
| XL2 | 23 | 1.00E-06 | 119 | 1.19E+09 | 91.54 |
| XL2 | 24 | 1.00E-06 | 130 | 1.30E+09 | 100.00 |
| XL2 | +ve | 1.00E-06 | 91 | 1.08E+09 | 83.08 |
| XL2 -veC | 11 | 1.00E-01 | 0 | 0 | |
| XL2 -veC | 15 | 1.00E-01 | 0 | 0 | |
| XL10 | 1 | 1.00E-06 | 0 | 0.00E+01 | 0.00 |
| XL10 | 3 | 1.00E-06 | 0 | 0.00E+01 | 0.00 |
| XL10 | 5 | 1.00E-06 | 0 | 0.00E+01 | 0.00 |
| XL10 | 7 | 1.00E-06 | 0 | 0.00E+01 | 0.00 |
| XL10 | 9 | 1.00E-06 | 39 | 3.90E+08 | 32.50 |
| XL10 | 11 | 1.00E-06 | 76 | 7.60E+08 | 63.33 |
| XL10 | 13 | 1.00E-06 | 66 | 6.60E+08 | 55.00 |
| XL10 | 15 | 1.00E-06 | 75 | 7.50E+08 | 62.50 |
| XL10 | 17 | 1.00E-06 | 67 | 6.70E+08 | 55.83 |
| XL10 | 19 | 1.00E-06 | 74 | 7.40E+08 | 61.67 |
| XL10 | 21 | 1.00E-06 | 52 | 5.20E+08 | 43.33 |
| XL10 | 23 | 1.00E-06 | 78 | 7.80E+08 | 65.00 |
| XL10 | 24 | 1.00E-06 | 64 | 6.40E+08 | 53.33 |
| XL10 | +ve | 1.00E-06 | 96 | 1.14E+09 | 95.00 |
| XL10 -veC | 13 | 1.00E-01 | 0 | 0.00E+01 | |
| XL10 -veC | 23 | 1.00E-01 | 2 | 2.00E+02 | |
| DH10B | 1 | 1.00E-06 | 0 | 0.00E+01 | 0.00 |

TABLE 1-continued

| Strain | Excipient* | Dilution | No. colonies | Cells/ml. | % survival |
|---|---|---|---|---|---|
| DH10B | 3 | 1.00E-06 | 0 | 0.00E+01 | 0.00 |
| DH10B | 5 | 1.00E-06 | 0 | 0.00E+01 | 0.00 |
| DH10B | 7 | 1.00E-06 | 0 | 0.00E+01 | 0.00 |
| DH10B | 9 | 1.00E-06 | 10 | 1.00E+08 | 18.18 |
| DH10B | 11 | 1.00E-06 | 17 | 1.70E+08 | 30.91 |
| DH10B | 13 | 1.00E-06 | 12 | 1.20E+08 | 21.82 |
| DH10B | 15 | 1.00E-06 | 14 | 1.40E+08 | 25.45 |
| DH10B | 17 | 1.00E-06 | 24 | 2.40E+08 | 43.64 |
| DH10B | 19 | 1.00E-06 | 54 | 5.40E+08 | 98.18 |
| DH10B | 21 | 1.00E-06 | 16 | 1.60E+08 | 29.09 |
| DH10B | 23 | 1.00E-06 | 39 | 3.90E+08 | 70.91 |
| DH10B | 24 | 1.00E-06 | 15 | 1.50E+08 | 27.27 |
| DH10B | +ve | 1.00E-06 | 66 | 7.86E+08 | 142.91 |
| DH10B -veC | 9 | 1.00E-01 | 0 | 0 | |
| DH10B -veC | 11 | 1.00E-01 | 0 | 0 | |

*Composition of excipient given in table 2.

TABLE 2

| Excipient | | DH109B | JM109 | XL2 | XL10 |
|---|---|---|---|---|---|
| 1 | 10% PVP | 0.00 | 0.00 | 0.00 | 0.00 |
| 3 | 10% PVP + 1% glycerol | 0.00 | 0.00 | 0.00 | 0.00 |
| 5 | 5% PVP | 0.00 | 0.00 | 0.00 | 0.00 |
| 7 | 5% PVP + 0.25% glycerol | 0.00 | 0.00 | 0.00 | 0.00 |
| 9 | 10% lactose | 18.18 | 40.00 | 67.69 | 32.50 |
| 11 | 10% lactose + 0.5% glycerol | 30.91 | 43.00 | 84.62 | 63.33 |
| 13 | 5% lactose | 21.82 | 41.00 | 80.77 | 55.00 |
| 15 | 5% lactose + 0.125% glycerol | 25.45 | 63.50 | 96.15 | 62.50 |
| 17 | 10% sucrose | 43.64 | 90.50 | 93.85 | 55.83 |
| 19 | 10% sucrose + 0.5% glycerol | 98.18 | 79.50 | 85.38 | 61.67 |
| 21 | 10% trehalose | 29.09 | 46.00 | 103.08 | 43.33 |
| 23 | 10% trehalose + 0.25% glycerol | 70.91 | 78.50 | 91.54 | 65.00 |
| 24 | 5% trehalose | 27.27 | 62.00 | 100.00 | 53.33 |
| +ve | +veC | 142.91 | 109.50 | 83.08 | 95.00 |

All publications mentioned in the above specification are herein incorporated by reference. Various modifications and variations of the described methods and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method for freeze-drying multiple samples of different viable microorganisms, which method comprises:
   (i) dispensing multiple liquid samples of a plurality of different microorganisms, each sample comprising a single, viable microorganism, into separate wells of a container comprising multiple wells;
   (ii) placing the container in a freeze-drying apparatus; and
   (iii) freeze-drying the samples present in the wells under conditions that substantially maintain the viability of the microorganisms.

2. The method according to claim 1 wherein the container is a microtiter plate.

3. The method according to claim 1 wherein the samples comprise an excipient.

4. The method according to claim 3 wherein the excipient is selected from the group consisting of lactose, sucrose and trehalose.

5. The method according to claim 3 wherein the viable microorganisms have been grown prior to freeze-drying in a culture medium comprising the excipient and the microorganisms are freeze-dried in said culture medium.

6. The method according to claim 1 which further comprises providing the wells of the container with sterile sealing means.

7. A container comprising multiple wells wherein the container houses multiple samples of different viable microorganisms, each well comprising a single, viable freeze-dried sample of a microorganism.

8. A container according to claim 7 which is a microtiter plate.

9. A container according to claim 7 which further comprises sterile sealing means for each well.

10. A container comprising multiple wells, each well comprising a viable freeze-dried sample of a microorganism obtained by the method of claim 1.

* * * * *